US011109995B1

(12) United States Patent
Anjonrin-Ohu et al.

(10) Patent No.: US 11,109,995 B1
(45) Date of Patent: Sep. 7, 2021

(54) SHOULDER SUPPORT SYSTEM

(71) Applicant: DeRoyal Industries, Inc., Powell, TN (US)

(72) Inventors: Olufunke Tina Anjonrin-Ohu, Knoxville, TN (US); Anna C. Mitchell, Knoxville, TN (US); Kathleen L. Parker, Knoxville, TN (US); Charles J. French, III, Fort Mill, SC (US)

(73) Assignee: DeRoyal Industries, Inc., Powell, TN (US)

( * ) Notice: Subject to any disclaimer, the term of this patent is extended or adjusted under 35 U.S.C. 154(b) by 473 days.

(21) Appl. No.: 15/875,022

(22) Filed: Jan. 19, 2018

(51) Int. Cl.
*A61F 5/37* (2006.01)

(52) U.S. Cl.
CPC .......... *A61F 5/3738* (2013.01); *A61F 5/3753* (2013.01)

(58) Field of Classification Search
CPC ...... A61F 5/373; A61F 5/3738; A61F 5/3746; A61F 5/3753; A61F 5/3723; A45C 9/00; A45F 3/02; A45F 2200/0516; A45F 2200/0525; A45F 2200/0558; A45F 2200/0575; A41D 13/0512
USPC ....................................................... 602/4, 20
See application file for complete search history.

(56) References Cited

U.S. PATENT DOCUMENTS

| 195,941 | A | | 10/1877 | McCabe | |
| 453,490 | A | | 6/1891 | Kropp | |
| 1,267,142 | A | | 5/1918 | Stowers et al. | |
| 1,304,153 | A | | 5/1919 | Bugge | |
| 1,808,422 | A | | 6/1931 | Macdonald | |
| 2,594,809 | A | | 4/1952 | Isador | |
| 2,856,919 | A | * | 10/1958 | Murray | A61F 13/04 602/12 |
| 3,103,216 | A | | 9/1963 | Scott | |
| 3,327,914 | A | | 6/1967 | Abram | |
| 3,404,680 | A | | 10/1968 | Guttman et al. | |
| 3,433,221 | A | | 3/1969 | Kendall et al. | |
| 4,232,664 | A | * | 11/1980 | Blatt | A61F 5/3738 602/4 |
| 4,355,635 | A | * | 10/1982 | Bihl | A61F 5/3738 128/DIG. 15 |
| 4,372,301 | A | | 2/1983 | Hubbard et al. | |
| 4,487,346 | A | | 12/1984 | Fischer, Jr. | |
| 4,598,703 | A | | 7/1986 | Lindemann | |
| 4,622,961 | A | | 11/1986 | Christensen | |
| 5,334,132 | A | | 8/1994 | Burkhead | |
| 5,569,172 | A | * | 10/1996 | Padden | A61F 5/3753 128/878 |
| 6,220,493 | B1 | * | 4/2001 | Iijima | A45F 3/00 224/153 |

(Continued)

*Primary Examiner* — Camtu T Nguyen
(74) *Attorney, Agent, or Firm* — Luedeka Neely Group, PC

(57) ABSTRACT

A shoulder support system includes an arm support configured for supporting an arm of a user; a convertible shoulder strap convertible between a loop configuration positionable around a shoulder of the user or as straight strap positionable to overlie the shoulder of the user; a front strap connectable between the convertible shoulder strap and a front of the arm support; and a rear strap connectable between the convertible shoulder strap and a rear of the arm support. The shoulder support may also include an abduction pad. In which case the arm support includes an elongate flexible extension affixed to the arm support and extendable outward from the arm support and positionable to be folded about the abduction pad.

9 Claims, 13 Drawing Sheets

(56) References Cited

U.S. PATENT DOCUMENTS

| | | | | |
|---|---|---|---|---|
| 6,311,884 B1* | 11/2001 | Johnson | ............... | A45F 3/04 |
| | | | | 224/153 |
| 7,563,236 B2 | 7/2009 | Kazmierczak et al. | | |
| 7,749,179 B2 | 7/2010 | Hargrave et al. | | |
| 8,414,512 B2* | 4/2013 | Fout | ............... | A61F 5/3753 |
| | | | | 128/869 |
| 8,746,523 B1* | 6/2014 | Woolley | ............... | A45C 13/30 |
| | | | | 224/578 |
| 2007/0261213 A1* | 11/2007 | Nolan | ............... | A45F 3/14 |
| | | | | 24/300 |
| 2008/0277434 A1* | 11/2008 | Sacks | ............... | A45C 13/30 |
| | | | | 224/153 |
| 2010/0116856 A1 | 5/2010 | Tompros et al. | | |
| 2014/0358052 A1* | 12/2014 | Cox | ............... | A61F 5/3738 |
| | | | | 602/4 |

\* cited by examiner

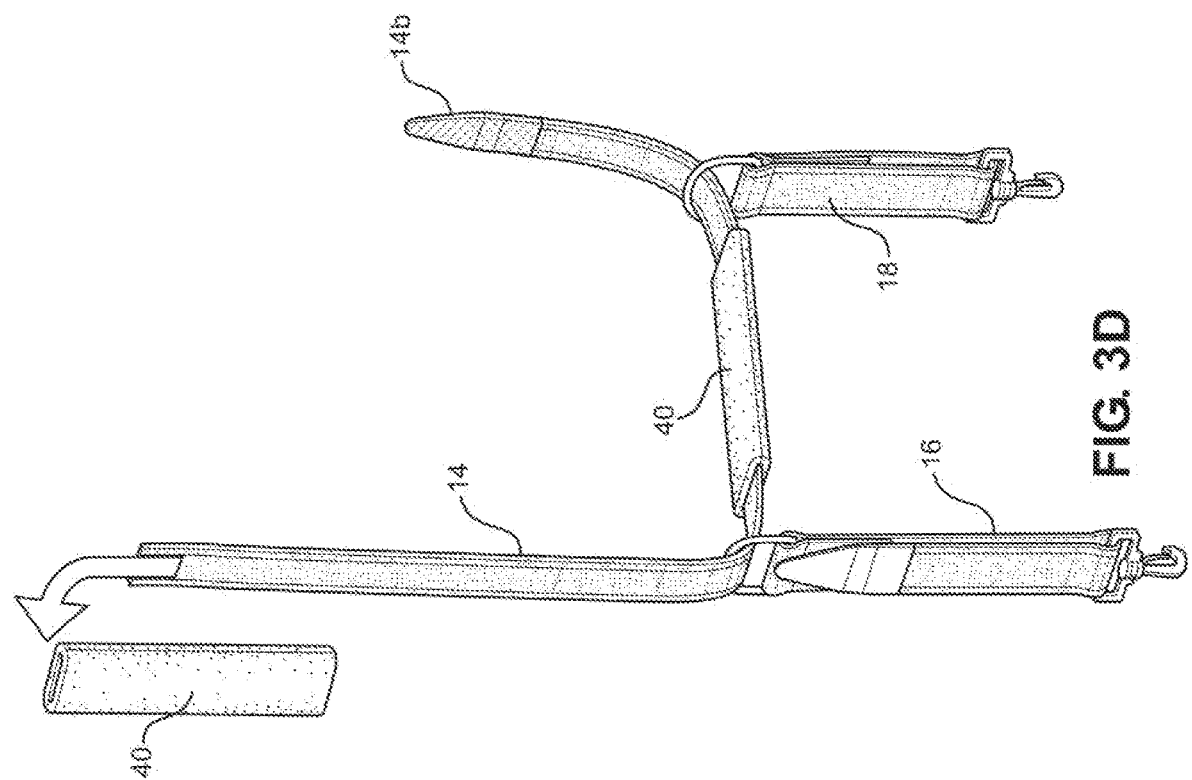
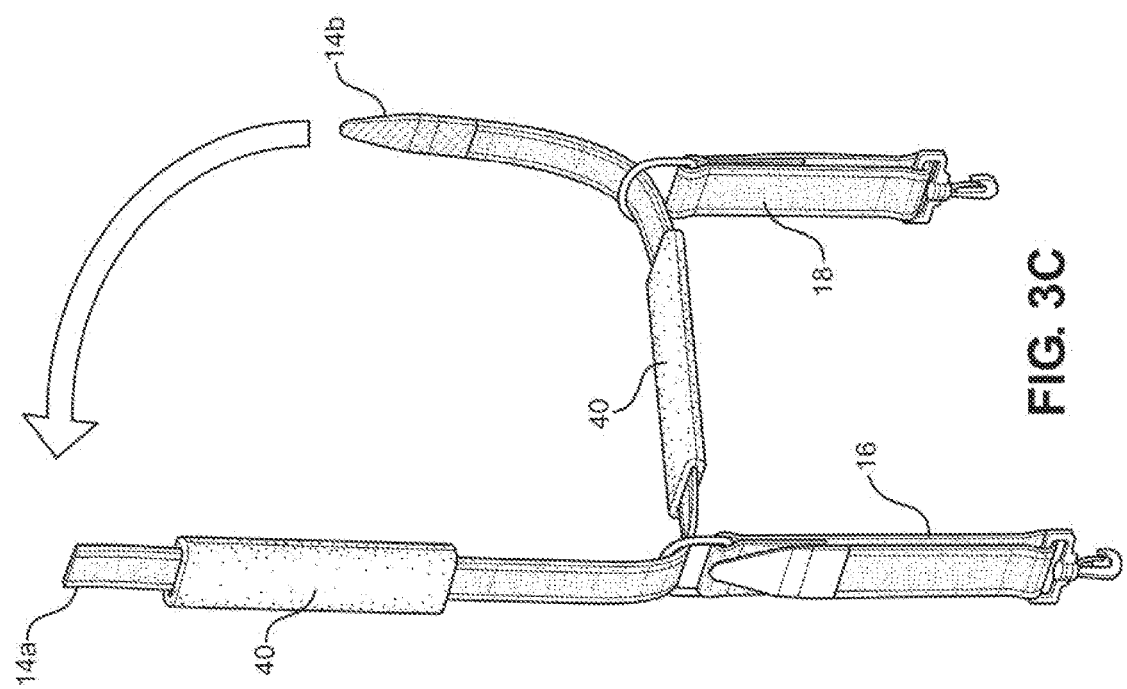
FIG. 3C
FIG. 3D

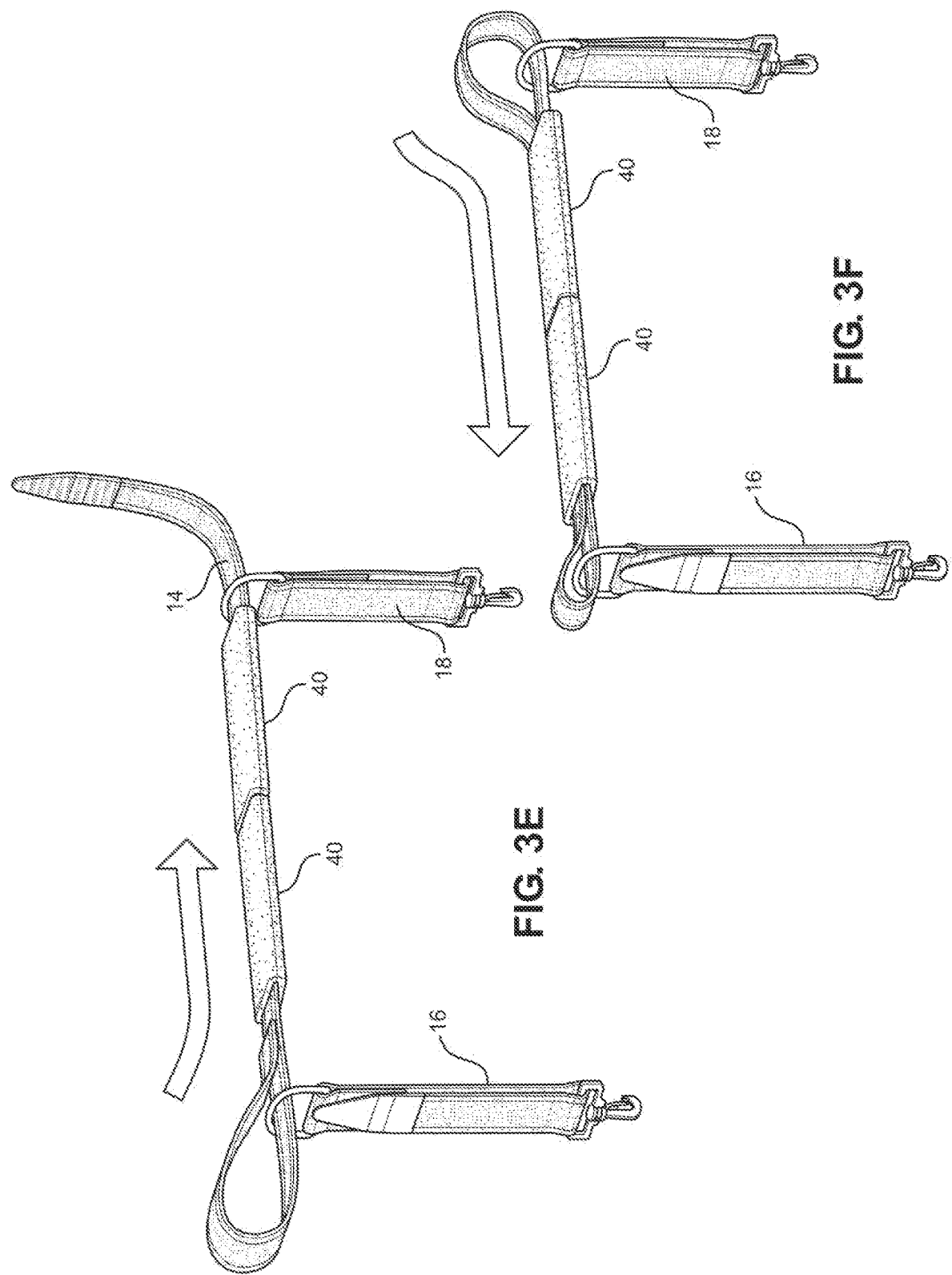

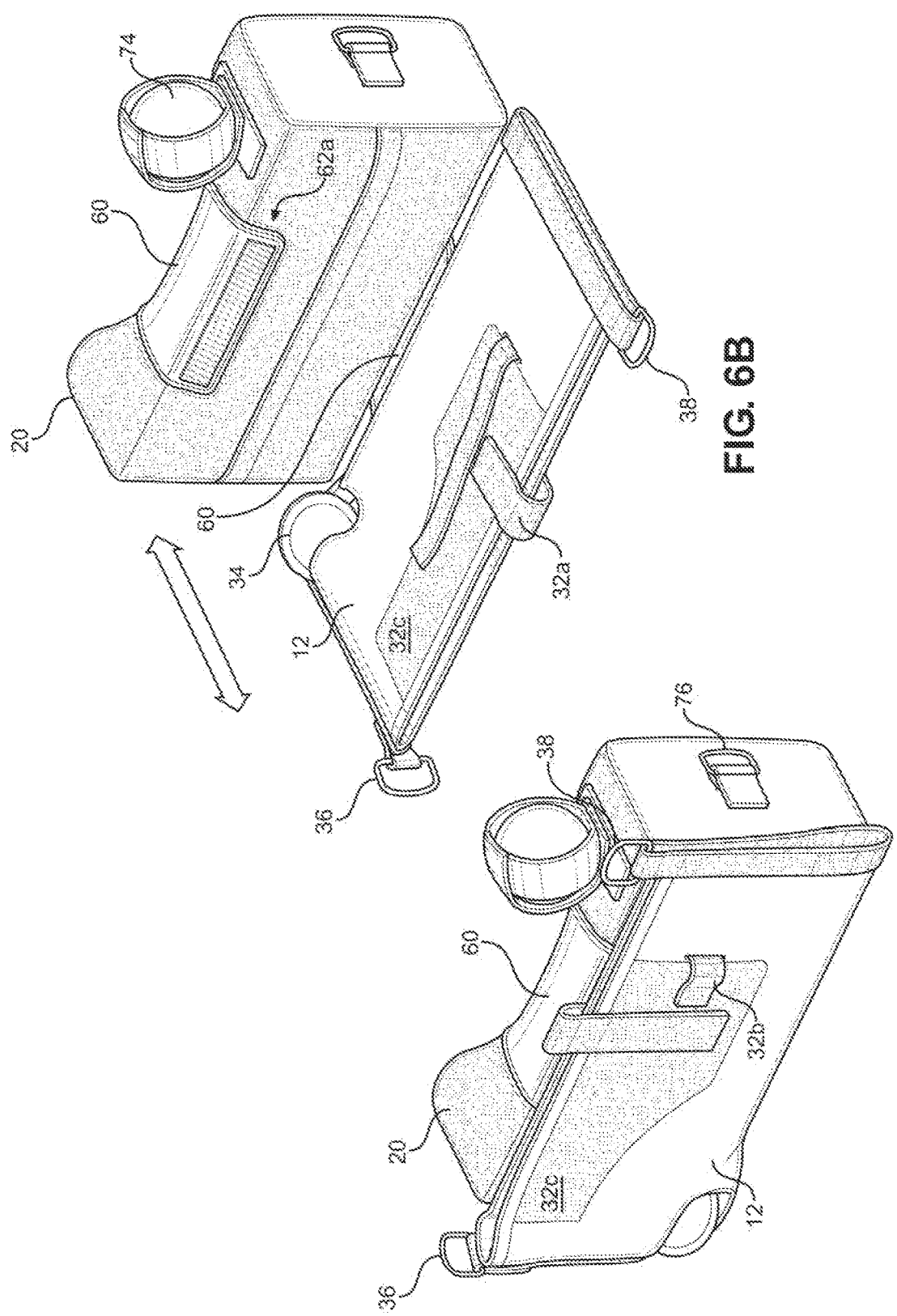

SHOULDER SUPPORT SYSTEM

FIELD

This disclosure relates to the field of shoulder supports. More particularly, this disclosure relates to shoulder supports that are easily converted to different configurations.

BACKGROUND

Improvement is desired in the provision of soft and flexible braces for supporting the shoulder. What is desired is a shoulder support that can easily be converted between different support configurations, while minimizing the number of components. Having multiple components increases both material and manufacturing costs and provides opportunity of loss or misplacement of components when they are not being utilized.

The present disclosure advantageously provides an improved shoulder support system that is convertible between different support configurations and overcomes disadvantages of prior shoulder support systems.

SUMMARY

The above and other needs are met by an improved shoulder support system. In one aspect, a shoulder support system according to the disclosure includes an arm support configured for supporting an arm of a user; a convertible shoulder strap convertible between a loop configuration positionable around a shoulder of the user or as straight strap positionable to overlie the shoulder of the user; a front strap connectable between the convertible shoulder strap and a front of the arm support; and a rear strap connectable between the convertible shoulder strap and a rear of the arm support.

In another aspect, a shoulder support system according to the disclosure includes an abduction pad; an arm support configured for supporting an arm of a user, the arm support including an elongate flexible extension affixed to the arm support and extendable outward from the arm support and positionable to be folded about the abduction pad; and fasteners located to secure the extension in place so that the extension remains folded about the abduction pad.

Shoulder supports according to the disclosure are advantageous as compared to prior devices. For example, the disclosure provides a shoulder support that can easily be converted between different support configurations, while minimizing the number of components. For example, in one aspect a single shoulder strap is provided, which may easily be converted between a circular loop to position around the shoulder or as straight strap to overlie the shoulder. Further, this conversion may be accomplished using all of the components associated with the shoulder strap, so that costs associated with manufacture are not increased, and the structure advantageously serves to avoid loss or misplacement of components when they are not being utilized.

In another aspect, the shoulder support provides a pouch structure that facilitates integration of an abduction pad, but which is also suitable for use without an abduction pad. The pouch structure enables use or non-use of a pad without needing assembly components that would tend to be lost or misplaced, depending on whether the pad is incorporated or not.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein:

FIGS. 3A-3H show conversion of the shoulder strap from the circular loop configuration to a straight strap configuration.

FIGS. 6A-6D show assembly of the abduction pad and arm pouch of the shoulder support system.

DETAILED DESCRIPTION

Figure 1:
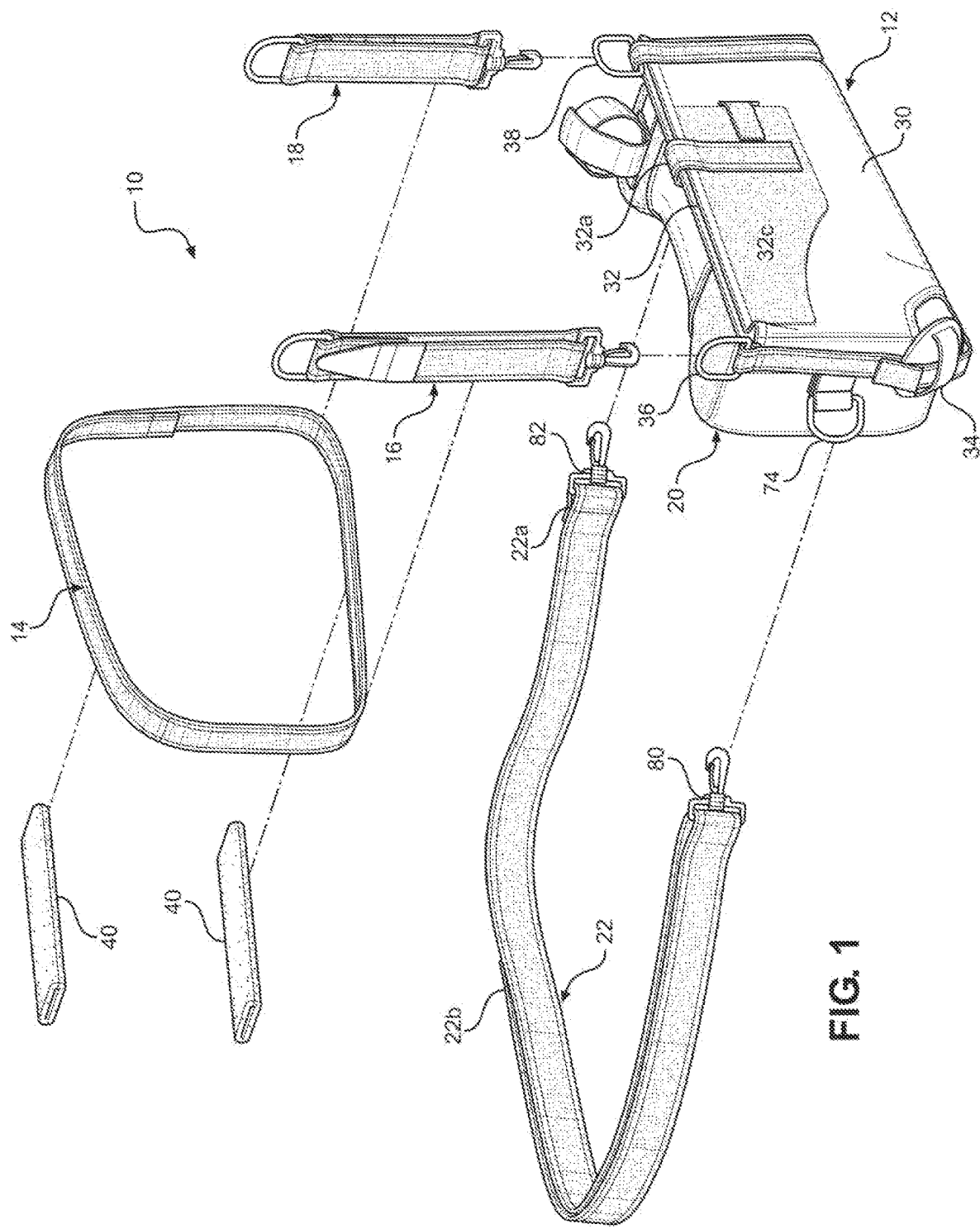
FIG. 1 is an exploded view of a shoulder support system according to the disclosure having a shoulder strap that may be configured as a circular loop to position around the shoulder or as a straight strap to overlie the shoulder.

With reference to the drawings, there is shown a shoulder support system 10. As seen in FIG. 1, shoulder support system 10 includes an arm support, such as a sling or pouch 12, a convertible flexible shoulder strap 14, a rear adjustable strap 16, and a front adjustable strap 18. The support system 10 also includes an abduction pad 20 and a waist belt 22, both or either of which may be removed and not used with the system if desired.

System 10 is configured to enable quick and easy configuration and reconfiguration of the support system while minimizing the number of components and reducing opportunity for loss or misplacement of components between the various configurations.

The system 10 also advantageously provides a universal fit for left and right injuries as well as patients of varying arm lengths. Shorter forearm lengths can be accommodated by rolling up the open edge of pouch 12 along the forearm length.

The pouch 12 may be of a variety of configurations suitable to provide a generally u-shaped support for placement of an arm, and preferably an elbow and forearm of a user. In this regard, the pouch 12 includes a u-shaped body 30 open at each end, and also preferably along an upper end 32 of the body 30. An upper end closure strap 32a having hook material compatible with loop material on the body 30 may be provided to enable full or partial closure of the upper end 32. An adjustable arm securement strap 32b runs from one side of the body 30 to the other, passing through the body 30 for securing the arm in place. The strap 32b may include hook material or other fastening structure at its ends to facilitate adjustment of the length and tension of the strap 32b. Loop material 32c or other fastener is located on the body 30 to cooperate with the straps 32a and 32b for adjustable securement thereof.

An elbow end of the body 30 may include an elbow support 34. The elbow support is configured as a bursitis pad, preferably a removable circular pad, that is included on a strap of the elbow support to offer additional cushion/comfort where bursitis may occur. An upper portion of the elbow end of the body 30 includes a fastener 36, such as a D-ring or other structure secured to the pouch 12 for releasably connecting the rear strap 16 to the pouch 12. An upper portion of an opposite front end of the body 30 includes a fastener 38, such as a D-ring or other structure secured to the pouch 12 for releasably connecting the front strap 18 to the pouch 12.

As described below in connection with FIGS. 6A-6D, the pouch 12 may include additional structure for facilitating easy and convenient installation of the pad 20 if it is desired to utilize the pad 20. The pouch 12, as configured, may be used with or without the pad 20, and without having components that could be easily lost or misplaced.

The convertible flexible shoulder strap 14 may be made of a single length of an elongate strap material, such as nylon or cotton strap material, having opposite ends 14a and 14b. The strap material may be of various materials and cross-sections, but a flat material is preferred for comfort. The strap 14 may include a hook or loop material thereon and the ends 14a and 14b configured to include a loop or hook material to facilitate releasably connection of the ends 14a and 14b to the strap 14 to maintain the strap 14 in the desired configuration. The end 14b is desirably tapered to facilitate conversion and use of the strap 14. The ends 14a and 14b One or more optional comfort sleeves 40 may be included with the shoulder strap 14 to enhance comfort. The sleeves 40 may be provided as by a neoprene or other cushioning material.

Figure 2:
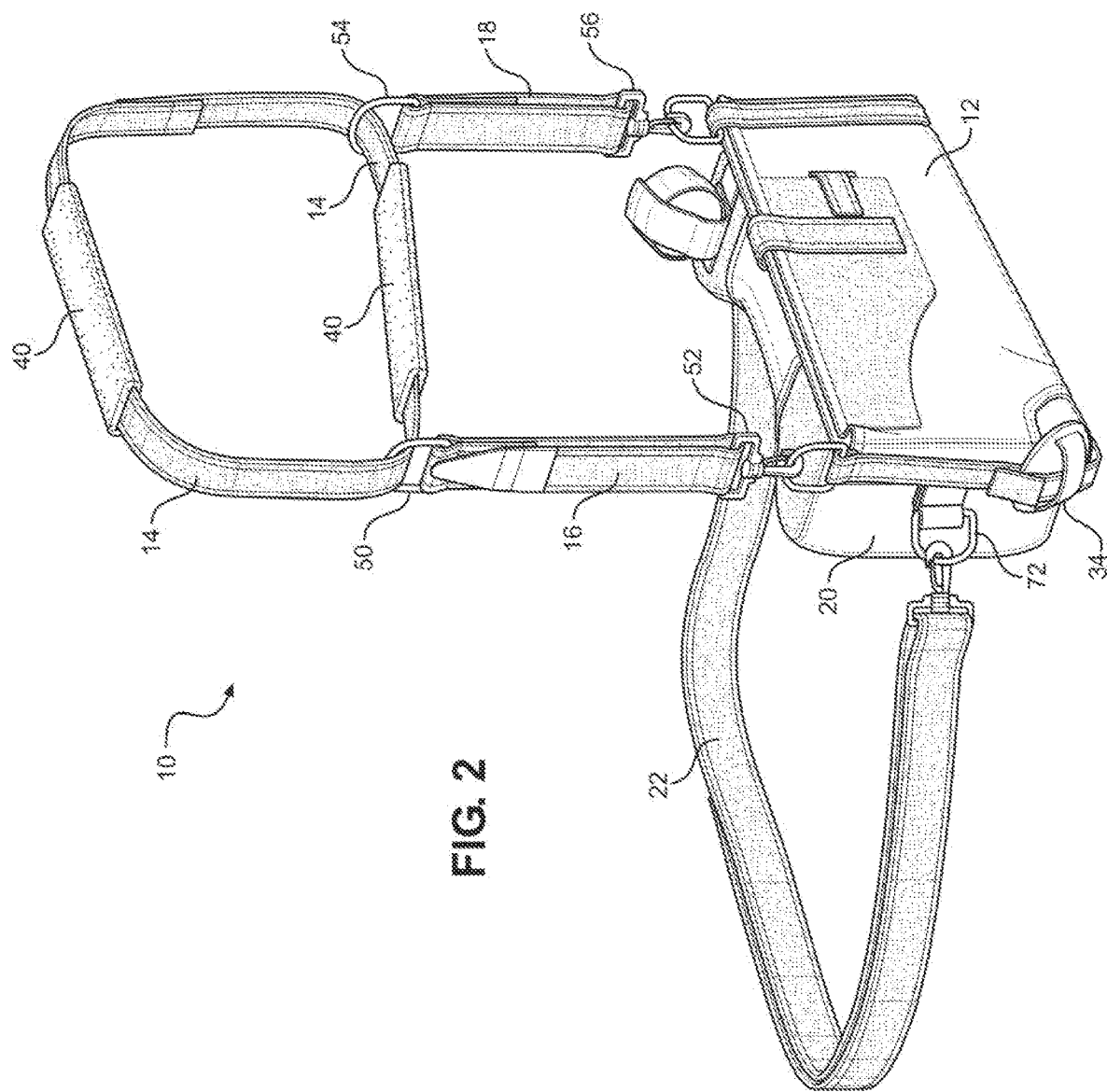
FIG. 2 shows the shoulder support with the shoulder strap configured as a circular loop to position around the shoulder.
Figure 3A:
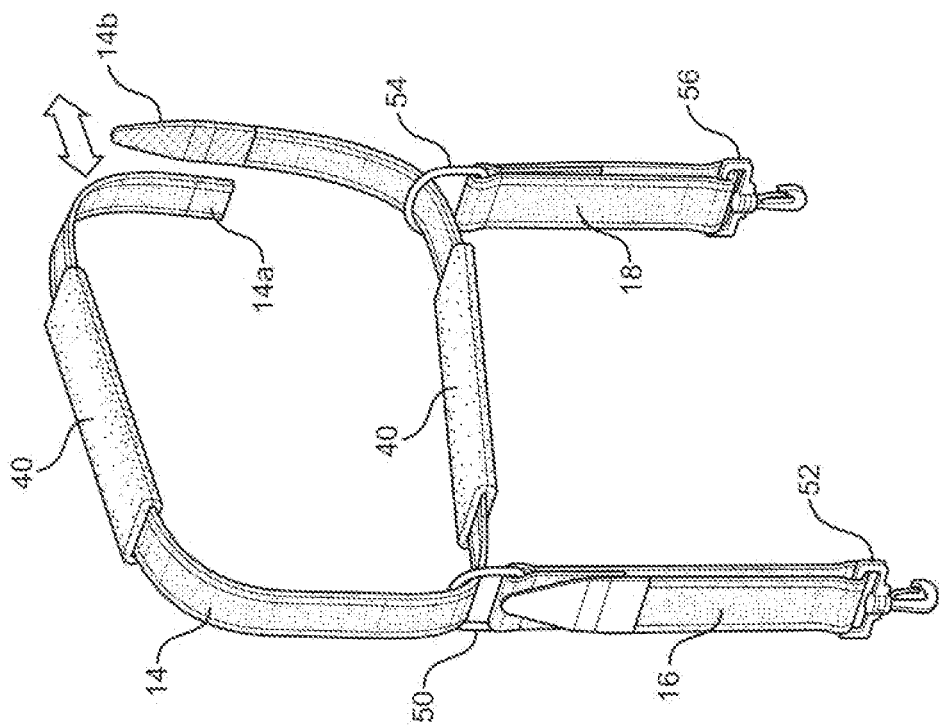
Figure 3B:
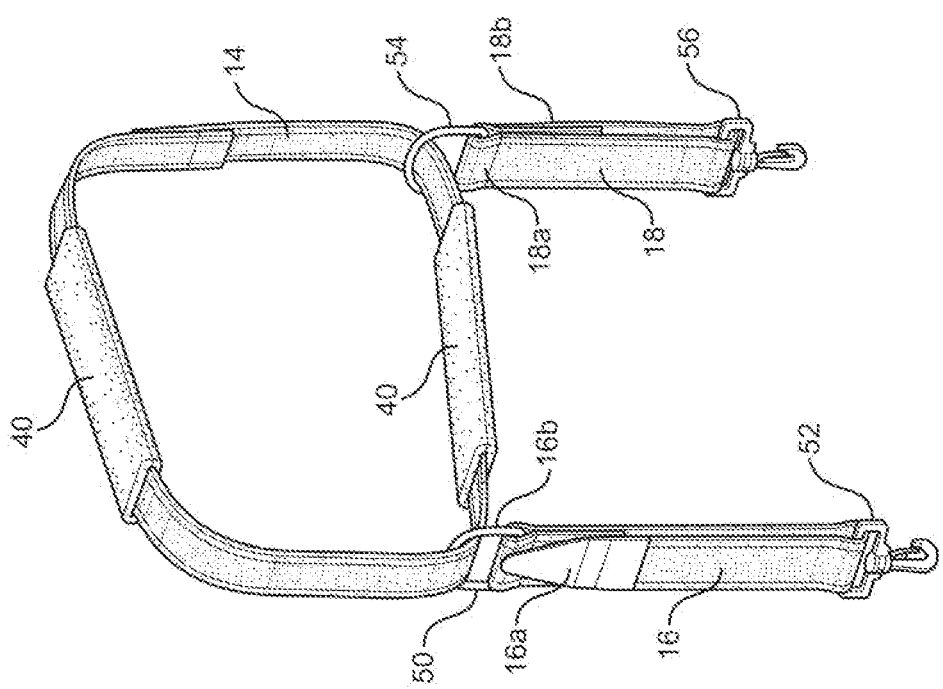
Figure 3H:
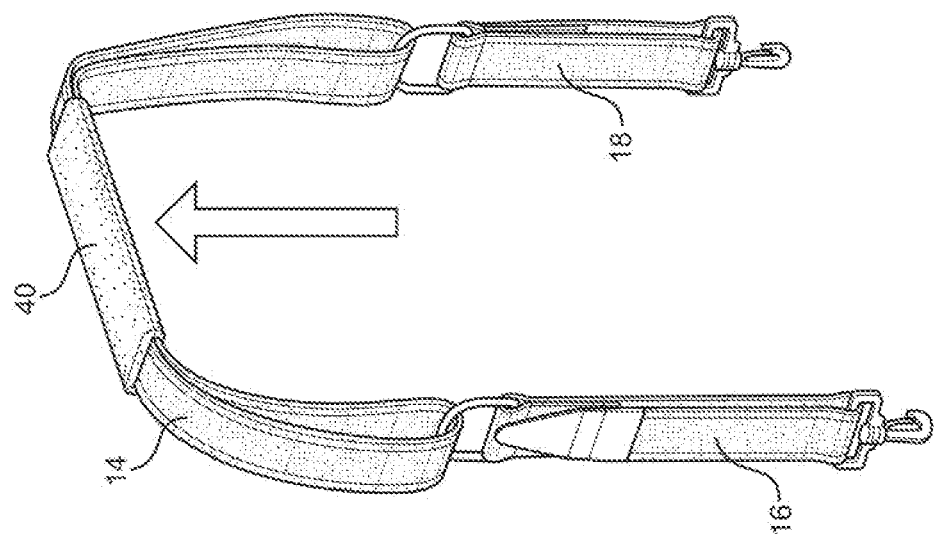
Figure 3G:
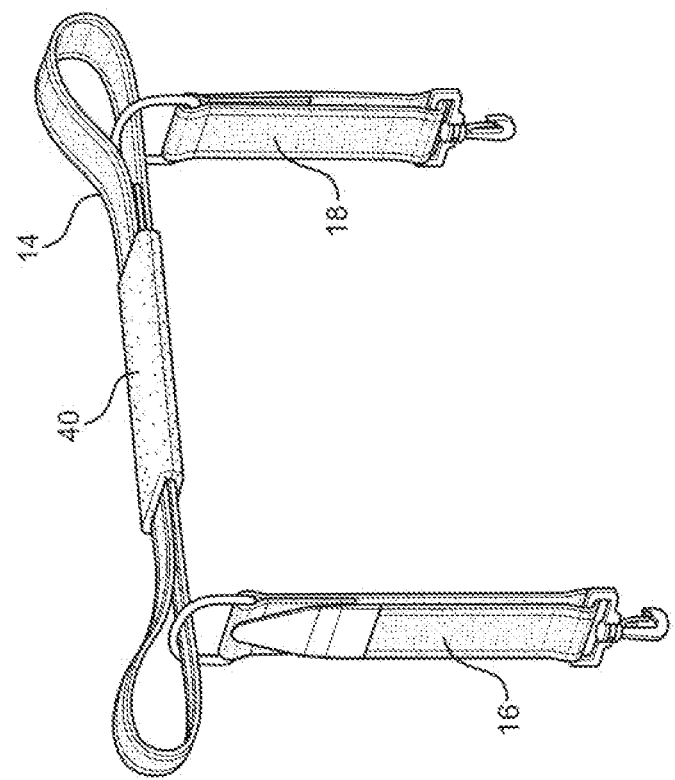

The shoulder strap 14 may be configured as a circular loop of adjustable diameter to position around the shoulder or as straight strap of adjustable length to overlie the shoulder of the user. In this regard, FIG. 2 shows the shoulder support 10 with the shoulder strap 14 configured as a circular loop to position around the shoulder. This configuration of the shoulder strap 14 further stabilizes the arm in the pouch 12 from movements as compared to use of the shoulder strap 14 in the straight configuration. This configuration of the shoulder strap 14 further stabilizes and offloads the weight of the arm in the pouch FIGS. 3A-3H show conversion of the shoulder strap 14 from the circular loop configuration to a straight strap configuration. The steps may be reversed to convert the strap 14 back to the circular loop configuration from the straight strap configuration. As shown, the ends 14a and 14b of the strap 14 are released from the strap 14, and the ends reattached to the strap 14 to provide the strap 14 in the desired length. The strap 14 is desirably threaded through the comfort sleeves 40, with the sleeves 40 located so as to overlie the shoulder of the user when the strap 14 is used in this configuration. This provides comfort and serves to avoid loss of the sleeves 40 as they are retained on the strap 14. FIG. 3H shows the strap 14 in the straight strap configuration.

The rear and front adjustable straps 16 and 18 connect between the convertible shoulder strap 14 and the arm pouch 12.

The rear adjustable strap 16 may be provided by a length of flexible strap material, such as nylon, having opposite ends 16a and 16b, with the end 16b desirably tapered. A D-ring 50 or like fastener is desirably fixed at the end 16a. The strap 16 may include a hook or loop material thereon and the end 16b configured to include a loop or hook material to facilitate releasably connection of the end 16b to the strap 16 to adjust and maintain the length of the strap 16. A swivel snap hook 52 having a ring for receiving the strap 16 and a swivel hook attached to the ring or like fastener is located along the length of the strap 16 and is configured to releasably attach to the fastener 36 at the rear of the pouch 12. The end 16b is desirably tapered.

The front adjustable strap 18 may be provided by a length of flexible strap material, such as nylon, having opposite ends 18a and 18b, with the end 18b desirably tapered. A D-ring 54 or like fastener is desirably fixed at the end 18a. The strap 18 may include a hook or loop material thereon and the end 18b configured to include a loop or hook material to facilitate releasably connection of the end 18b to the strap 18 to adjust and maintain the length of the strap 18. A swivel snap hook 56 having a ring for receiving the strap 18 and a swivel hook attached to the ring or like fastener is located along the length of the strap 18 and is configured to releasably attach to the fastener 38 at the rear of the pouch 12.

Figure 4B:
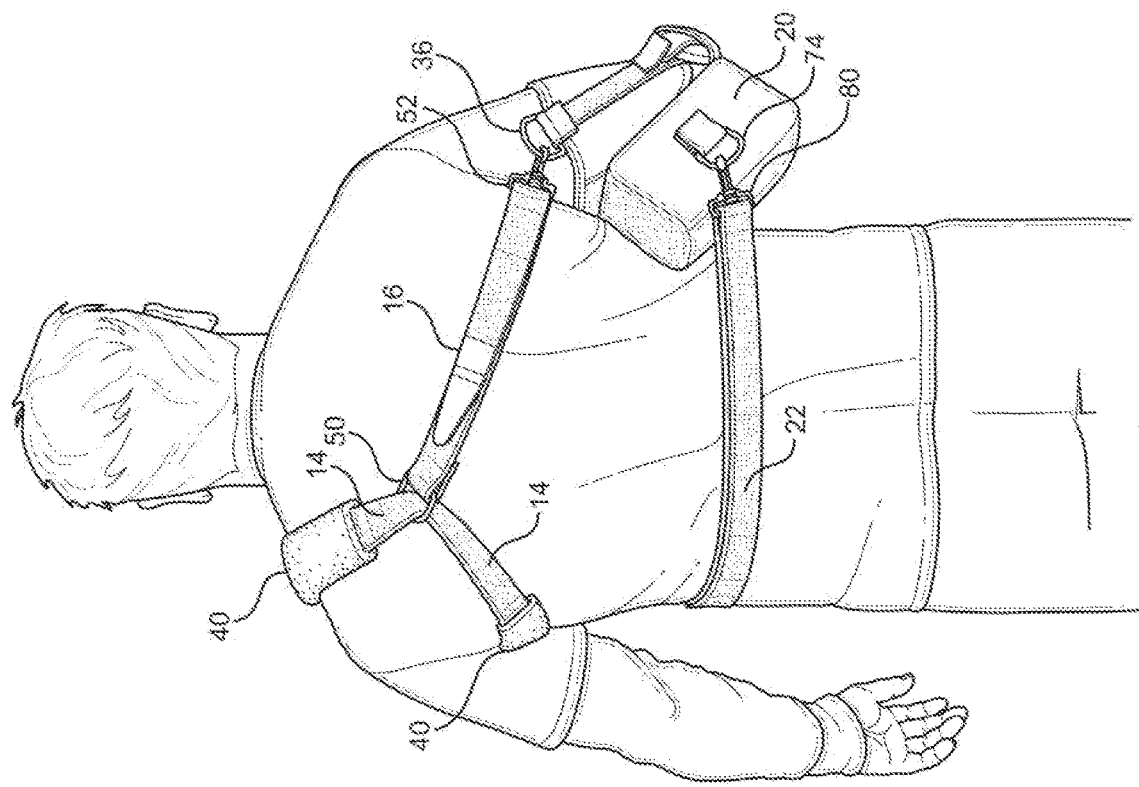
FIGS. 4A and 4B are anterior and posterior views, respectively, that show the shoulder support with the shoulder strap configured as a circular loop to position around the left shoulder of a user.
Figure 4A:
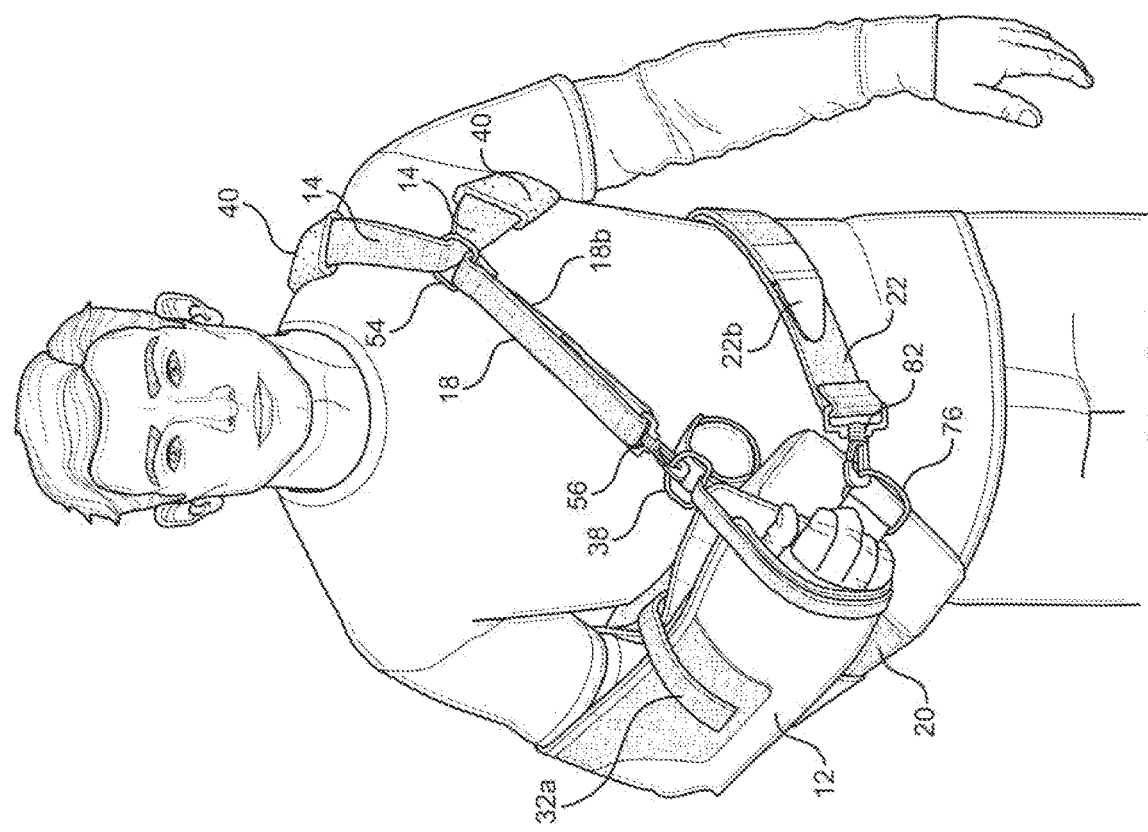
Figure 4C:
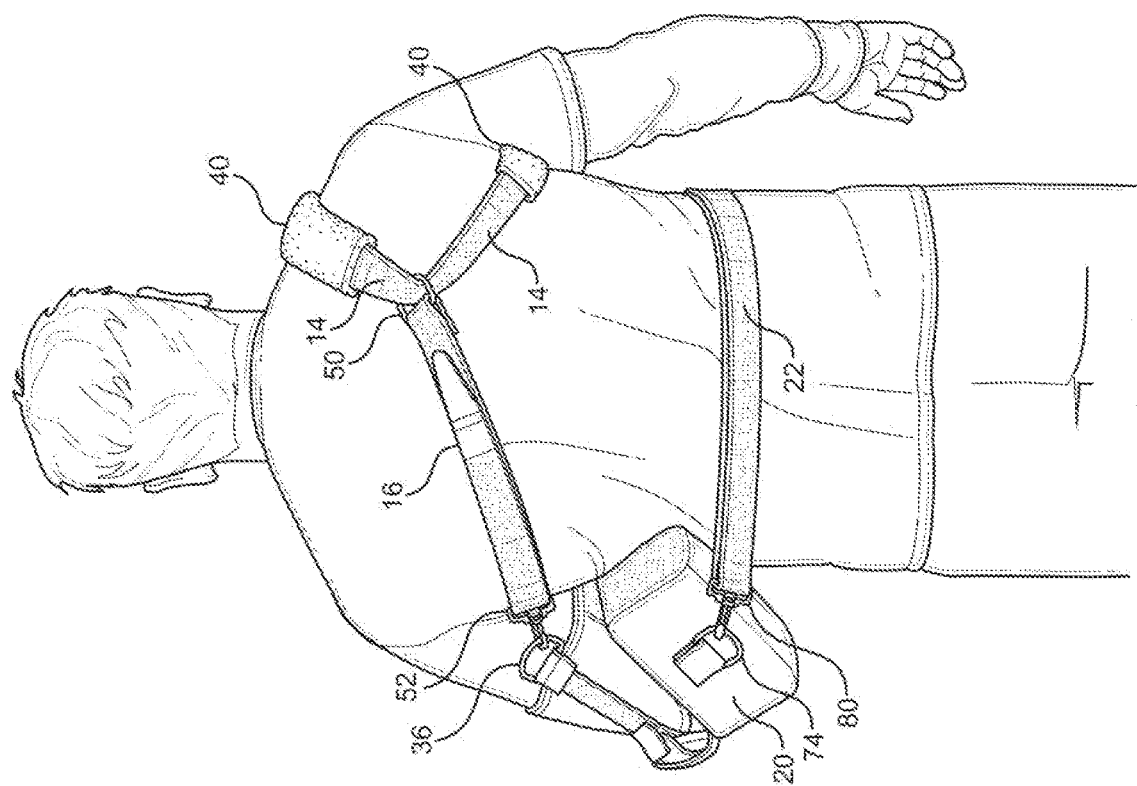
FIGS. 4C and 4D show installation on the opposite side.
Figure 4D:
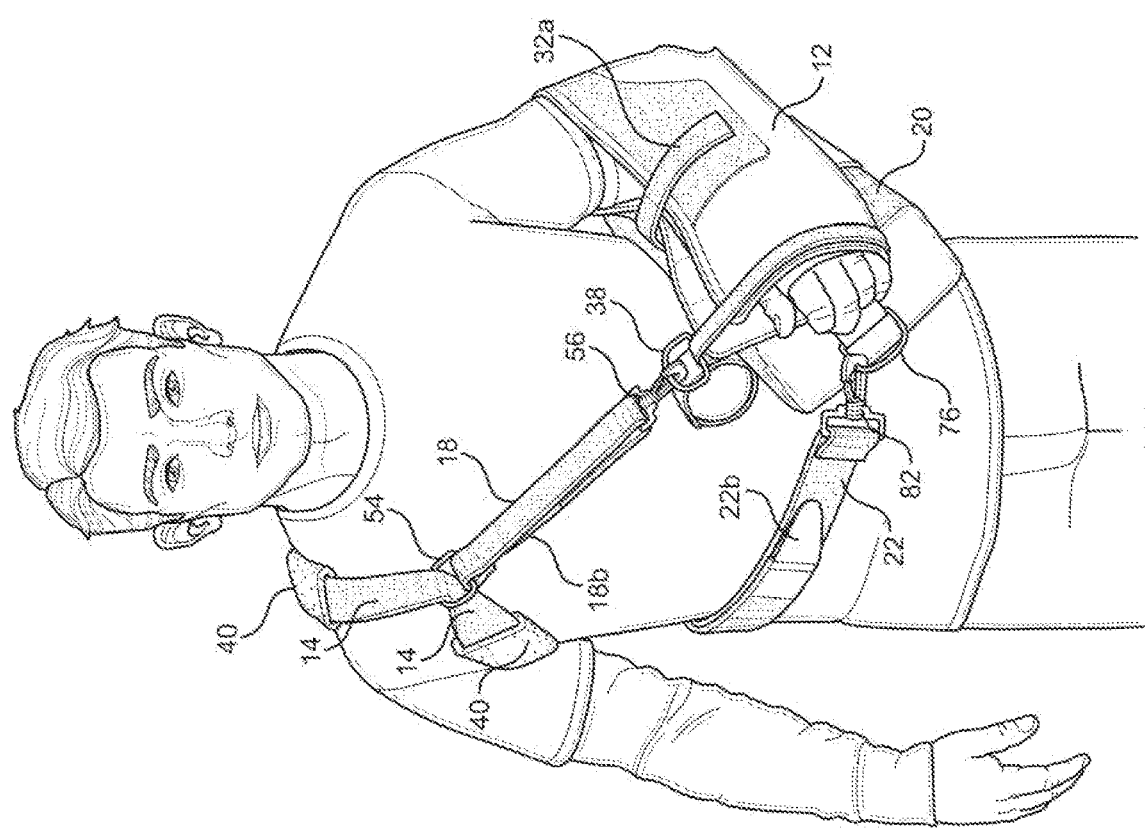

FIGS. 4A and 4B are anterior and posterior views, respectively, that show the shoulder support 10 with the right arm in the pouch 12 and the shoulder strap 14 configured as a circular loop to position around the left shoulder, installed onto a user. FIGS. 4C and 4D show the shoulder support installed on the opposite arm and shoulder. Thus, it will be appreciated that the shoulder system 10 is easily converted so as to be installed on either side of the user.

Figure 5A:
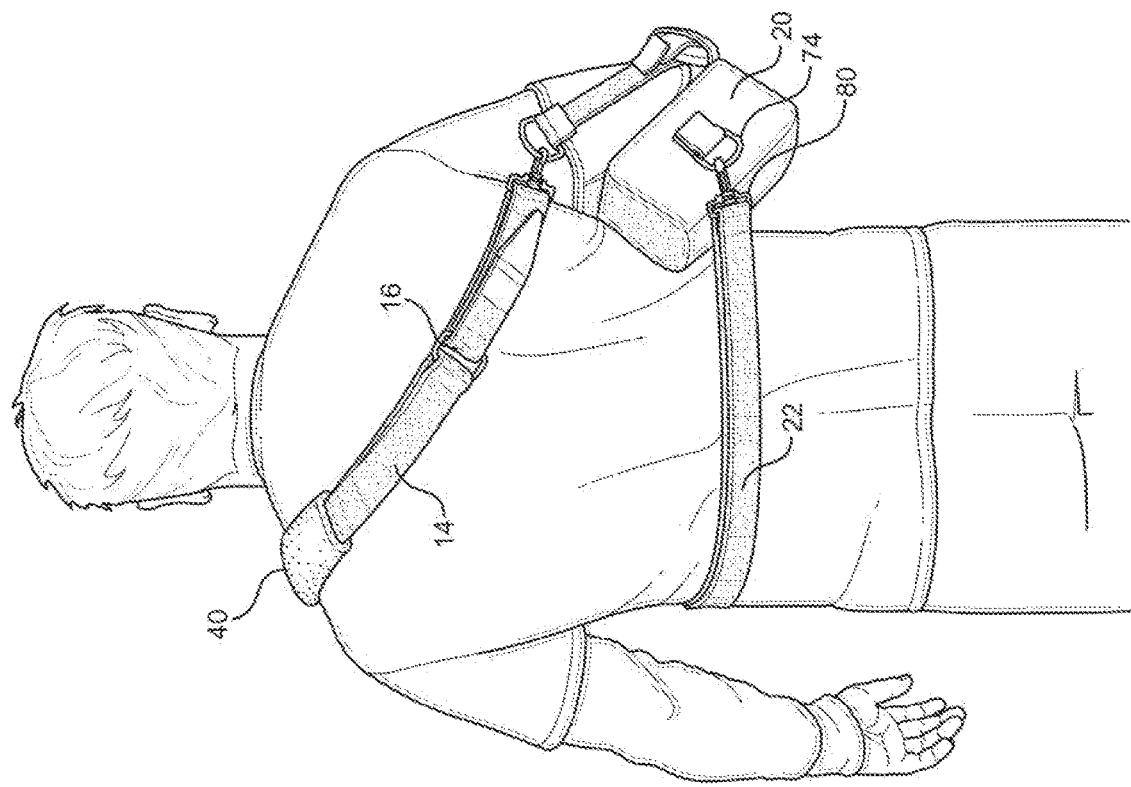
FIGS. 5A and 5B are anterior and posterior views, respectively, that show the shoulder support with the shoulder strap configured as a straight strap to overlie the left shoulder of a user.
Figure 5B:
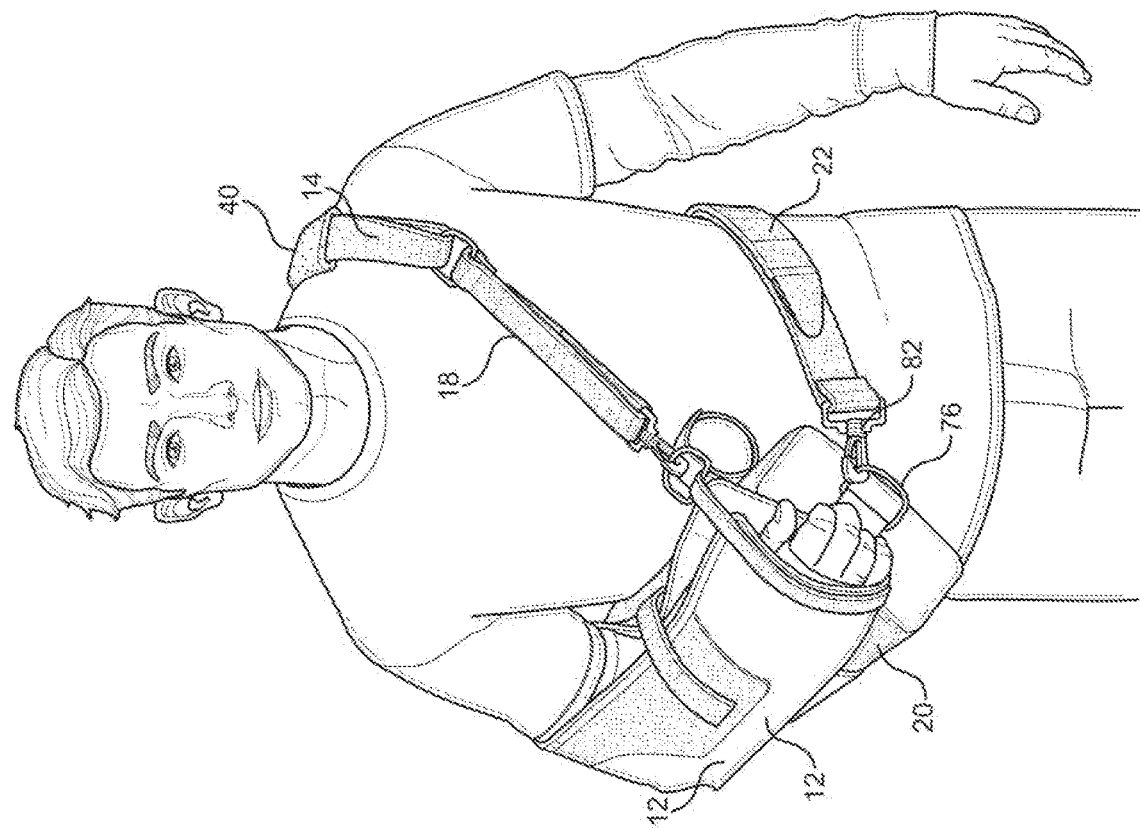
Figure 5C:
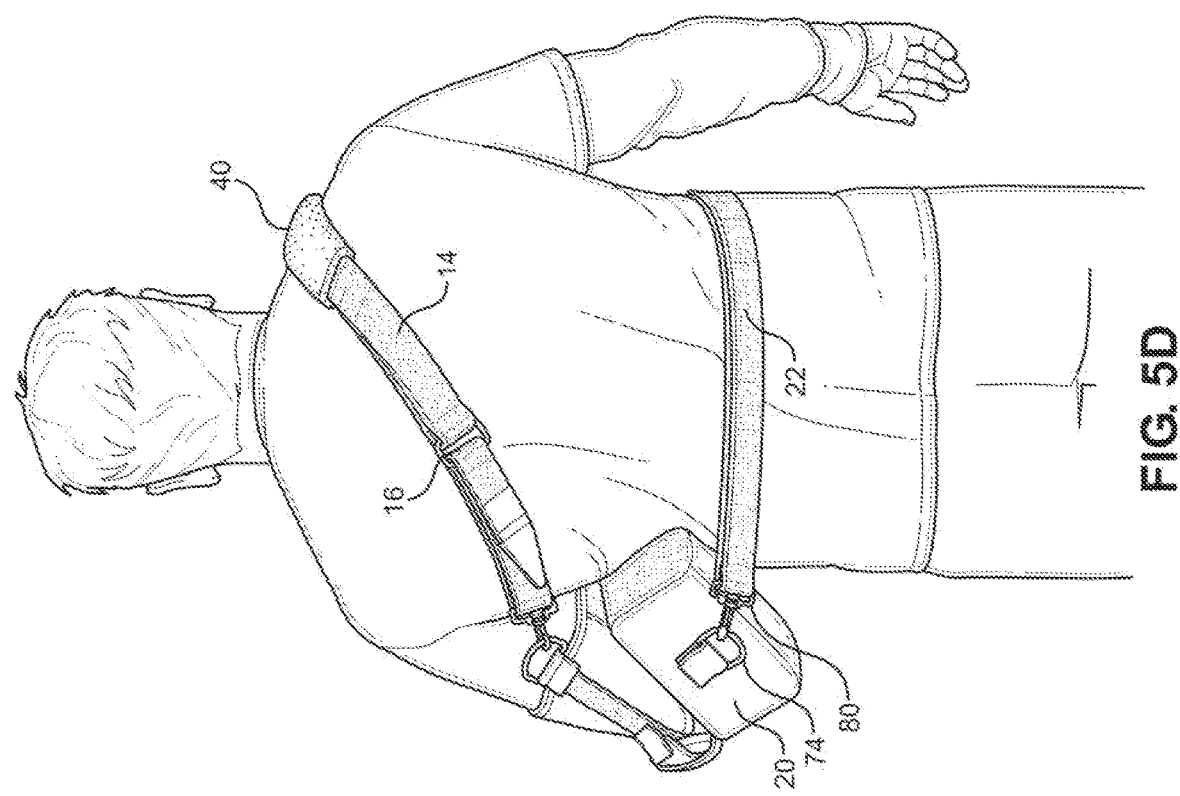
FIGS. 5C and 5D show installation on the opposite side.
Figure 5D:
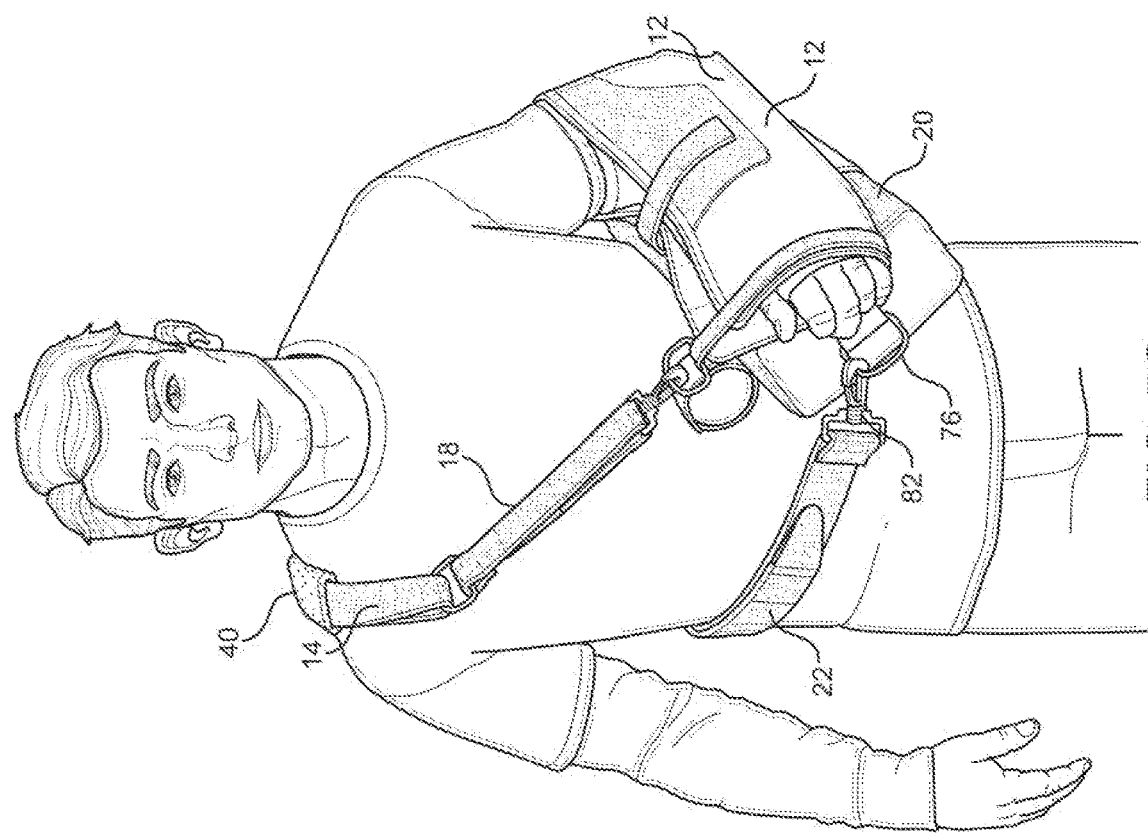
Figure 6C:
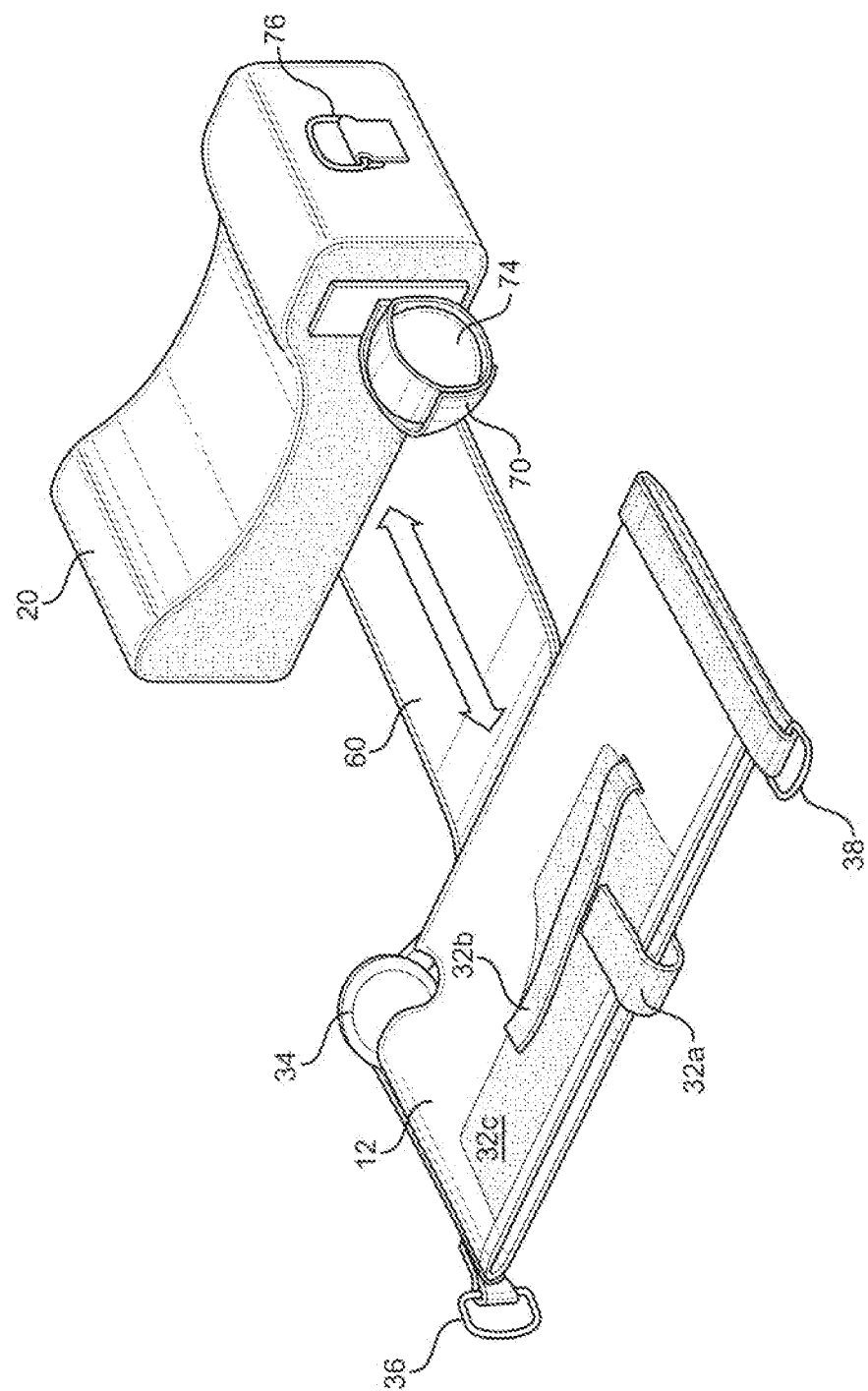
Figure 6D:
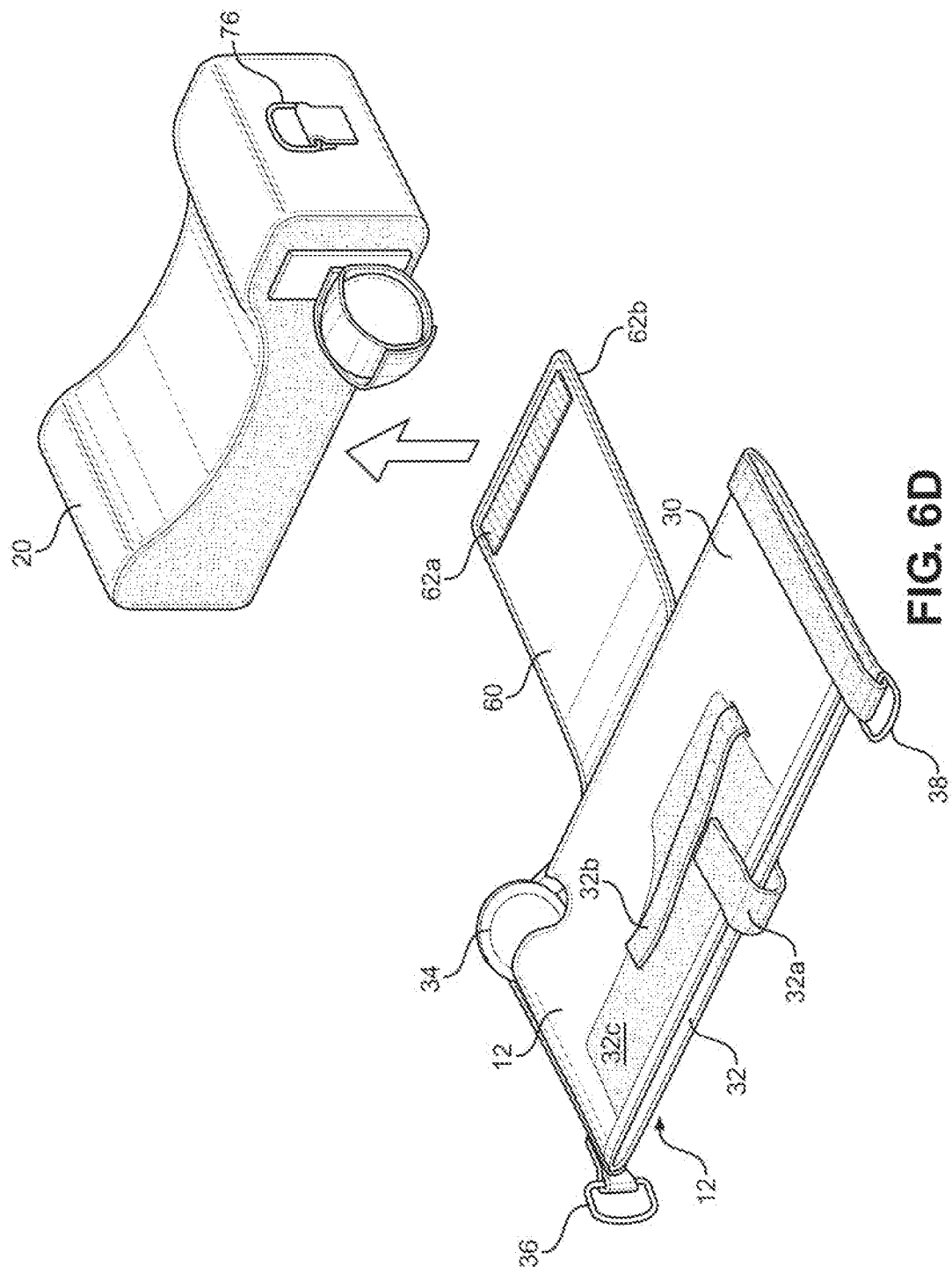

FIGS. 5A and 5B are anterior and posterior views, respectively, that show the shoulder support oriented with the right arm in the pouch 12 with the shoulder strap 14 configured as a straight strap to overlie the left shoulder installed onto a user. FIGS. 5C and 5D show the shoulder support installed on the opposite arm and shoulder.

With additional reference to FIGS. 6A-6D, the pouch 12, in addition to the previously described components, is configured to facilitate integration and desired positioning of the pad 20 to abduct the arm away from the body. Conventional pads and pouches are often undesirably positioned relative to one another such that the pad is used as an arm rest under the pouch. This is undesirable and the pouch 12 is configured to properly position the pad 20 to abduct the arm away from the body and prevent use of the pad 20 as an arm rest under the arm.

In this regard, the pouch 12 includes an elongate flexible extension 60. The extension 60 is desirably affixed, as by stitches, to a lower edge of the pouch 12. The extension 60 is of sufficient length to fold around the pad 20 as shown. The extension 60 includes near its distal end a hook material or other fastener 62a on one side, and a hook material or other fastener 62b on the opposite side. The fastener 62a is releasably connectable to the pad 20, as by mating with loop material on the pad 20 or other fastener thereon. The fastener 62b is connectable to the loop material or other fastener 32c on the proximate side of the body 30 of the pouch 12 as shown.

It will be appreciated that the pouch 12 and the pad 20 are configured so that the pouch 12 and the pad 20 may be utilized on either side of the patient. That is, with the left arm and side of the patient or the right arm and side of the patient.

The abduction pad 20 is provided as by a foam pad body or the like configured as shown to curve around the torso of the user. The pad body is covered with a loop fabric material that mates with the hook material 62a and facilitates integration of the pad 20 with the pouch 12. A receiver 70 may be provided as by straps of cooperating hook and loop material for maintaining a squeezable therapy ball 72 or the like proximate the hand of the user. A D-ring 74 or other fastener is attached to the rear of the pad 20 and a D-ring 76 or other fastener is attached to the front of the pad 20 for cooperating with the waist belt 22.

The waist belt 22 may be provided by a length of flexible strap material, such as nylon, having opposite ends 22a and 22b. The end 22b is desirably tapered. The strap 22 may include a hook or loop material thereon and the end 22b configured to include a loop or hook material to facilitate releasably connection of the end 22b to the strap 22 to adjust and maintain the length of the strap 22. A swivel snap hook 80 having a ring for receiving the strap 22 and a swivel hook attached to the ring or like fastener is locatable along the strap 22 to attach to the D-ring 74 of the pad 20. A swivel snap hook 82 is located at the end 22a and configured to attach to the D-ring 76 of the pad 20.

The system 10 provides a shoulder support that can easily be converted between different support configurations, while minimizing the number of components. For example, in one aspect a single shoulder strap is provided, which may easily be converted between a circular loop to position around the shoulder or as straight strap to overlie the shoulder. Further, this conversion may be accomplished using all of the components associated with the shoulder strap, so that costs associated with manufacture are not increased, and the structure advantageously serves to avoid loss or misplacement of components when they are not being utilized. The system 10 may also easily be converted for use on either side of the user.

The system 10 also advantageously provides a pouch structure that facilitates integration of an abduction pad, and facilitates use of the pouch and the pad on either side of the patient.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

The invention claimed is:

1. A shoulder support system, comprising:
   an arm support configured for supporting an arm of a user;
   a shoulder strap being convertible between a loop configuration in which the shoulder strap is adapted to encircle a shoulder of the user so as to extend above the shoulder and under an arm pit of the user, and a straight configuration in which the shoulder strap is adapted to extend above and overlie the shoulder of the user;
   a front strap connectable between the convertible shoulder strap and a front of the arm support; and
   a rear strap connectable between the convertible shoulder strap and a rear of the arm support.

2. The system of claim 1, wherein the front strap comprises an adjustable length strap.

3. The system of claim 1, wherein the rear strap comprises an adjustable length strap.

4. The system of claim 1, wherein the front strap or the rear strap or both the front strap and the rear strap further include a swivel connected thereto, the swivel included on the front strap located between the front strap and the arm support and the swivel included on the rear strap located between the rear strap and the arm support.

5. The system of claim 1, wherein the shoulder strap enables the loop configuration to be adjustable in diameter and the straight configuration to be adjustable in length.

6. The system of claim 1, wherein the shoulder strap comprises a single length of material.

7. The system of claim 1, wherein the system further includes an abduction pad and the arm support includes an elongate flexible extension affixed to the arm support and extendable outward from the arm support and positionable to be folded about the abduction pad.

8. A shoulder support system for a user having a left arm and left side and a right arm and right side, the shoulder support system, comprising:
   an abduction pad configured for use on either the left side or the right side of the user;
   an arm support comprising a pouch having a u-shaped body configured for supporting either the left arm or the right arm of the user, the arm support including an elongate flexible extension affixed to a lower portion of the arm support and extendable outward from the lower portion of the arm support and positioned to be folded to extend from the lower portion of the arm support around a lower side of the abduction pad and about a side of the abduction pad opposite the arm support; and
   fasteners located to secure the elongate flexible extension in place so that the elongate flexible extension remains folded about the abduction pad.

9. The system of claim 8, further comprising a shoulder strap being convertible between a loop configuration in which the shoulder strap is adapted to encircle a shoulder of the user so as to extend above the shoulder and under an arm pit of the user, and a straight configuration in which the shoulder strap is adapted to extend above and overlie the shoulder of the user; a front strap connectable between the shoulder strap and a front of the arm support; and a rear strap connectable between the shoulder strap and a rear of the arm support.

* * * * *